United States Patent
Ehlers et al.

(10) Patent No.: US 9,730,823 B2
(45) Date of Patent: Aug. 15, 2017

(54) RAPIST IDENTIFIER CUM RAPE VICTIM PROTECTOR

(71) Applicants: Sonette Elizabeth Ehlers, Warrenton (ZA); Vincent Edmund Leskowich, Dodecanes (GR)

(72) Inventors: Sonette Elizabeth Ehlers, Warrenton (ZA); Vincent Edmund Leskowich, Dodecanes (GR)

(*) Notice: Subject to any disclaimer, the term of this patent is extended or adjusted under 35 U.S.C. 154(b) by 92 days.

(21) Appl. No.: 14/386,782

(22) PCT Filed: Mar. 20, 2013

(86) PCT No.: PCT/ZA2013/000016
§ 371 (c)(1),
(2) Date: Sep. 19, 2014

(87) PCT Pub. No.: WO2013/142882
PCT Pub. Date: Sep. 26, 2013

(65) Prior Publication Data
US 2015/0027452 A1 Jan. 29, 2015

(30) Foreign Application Priority Data
Mar. 20, 2012 (ZA) .................. 2011/04519

(51) Int. Cl.
*A61F 5/00* (2006.01)
*A61F 5/455* (2006.01)
*A61B 5/117* (2016.01)

(52) U.S. Cl.
CPC ............ *A61F 5/0096* (2013.01); *A61B 5/117* (2013.01); *A61F 5/4553* (2013.01)

(58) Field of Classification Search
CPC ... A61F 5/00; A61F 5/0096; A61D 1/06; A61D 7/00; F41B 15/00
USPC ....................................... 128/844
See application file for complete search history.

(56) References Cited

FOREIGN PATENT DOCUMENTS

WO    WO 2011130756 A2 * 10/2011 ........... A61F 5/0096

* cited by examiner

*Primary Examiner* — Ophelia A Hawthorne
(74) *Attorney, Agent, or Firm* — William S. Parks

(57) ABSTRACT

A rapist identifier cum rape victim protector is provided. Such a device is of a flexible sheath of liquid impermeable condom type substance that is divided into a tissue attachment means carrying section extending from a mouth and a concertina effect formed inner end section. Attachment means in the form of tines are carried along a carrier base that is constituted from zigzag formed coaxially arranged members that are spaced apart by linear spacers from which the tines extend. The tines and base form a carrier body that forms part of the section to the effect of enabling its expansion once exposed to an action of sheath penetration. The tines are formed to require professional assistance for the release of the identifier cum protector once having become attached to a penetrating member.

19 Claims, 4 Drawing Sheets

RAPIST IDENTIFIER CUM RAPE VICTIM PROTECTOR

CROSS-REFERENCE TO RELATED APPLICATIONS

This application is a National Phase filing of Patent Cooperation Treaty Application No. PCT/ZA13/00016, accorded an international filing date of Mar. 20, 2013, which is based upon South African Patent Application No. 2011/04519, filed on Mar. 20, 2012. The entirety of the prior applications are thus incorporated by reference.

BACKGROUND TO THE INVENTION

The tracing of the committers of sexual crimes and especially rape is often a difficult task as no hidden motive can often be identified that can be used for investigation. As a result the perpetrators of such offences can be emboldened and proceed with a whole campaign before being caught. Being caught early on in a campaign will serve the end of justice while it will also deter would be perpetrators from committing such acts.

FIELD OF THE INVENTION

This invention relates to a sexual misconduct perpetrator identifier for use in identifying a sexual misconduct involving perpetrator. In addition to serving an identifying function the equipment can preferably also serve a protecting function thus being in the form of a sexual misconduct perpetrator identifier cum victim body protector. While not so limited the invention is particularly useful in protecting a rape victim and in identifying the perpetrator thus bringing rapists to justice while protecting persons exposed to such conduct.

PRIOR ART DESCRIPTION

Equipment used for protecting a female person against rape by way of location along the vagina is known in the art. U.S. Pat. No. 5,769,090 deals with a device that can send out a signal when penetration is perceived. The device also provides a needle that amongst others, penetrate the glans of the penis of a perpetrator. Such action is dangerous for the perpetrator even possibly resulting in death. As the device is visible to the perpetrator this can cause pre-rape violence. The devices of U.S. Pat. Nos. 5,353,811 and 6,250,304 also have the drawback that the glans is penetrated by spears or prongs with the same consequence as under the first mentioned patent. The device of U.S. Pat. No. 5,353,811 also holds the danger of blood from the perpetrator being released within the victim. South African patent number 2007/2952 discloses a rape victim protector and rapist identifier that includes penetrating tines but that does not easily accommodate a variety of penetrating member sizes while also holding the possibility of easily causing the tines to damage the sheath within which held while also not adequately firmly held to limit tine skewing during use of the equipment. Except for limiting the possibility of sheath damaging by the tines the same problems is experienced by the invention SA patent number 2007/2952 is found in the invention of PCT/ZA2008/00068.

BRIEF DESCRIPTION OF THE DRAWING

The invention is now described in more detail, by way of example, with reference to the accompanying drawings. In the drawings.

DETAILED DESCRIPTION OF THE DRAWING

Figure 1:
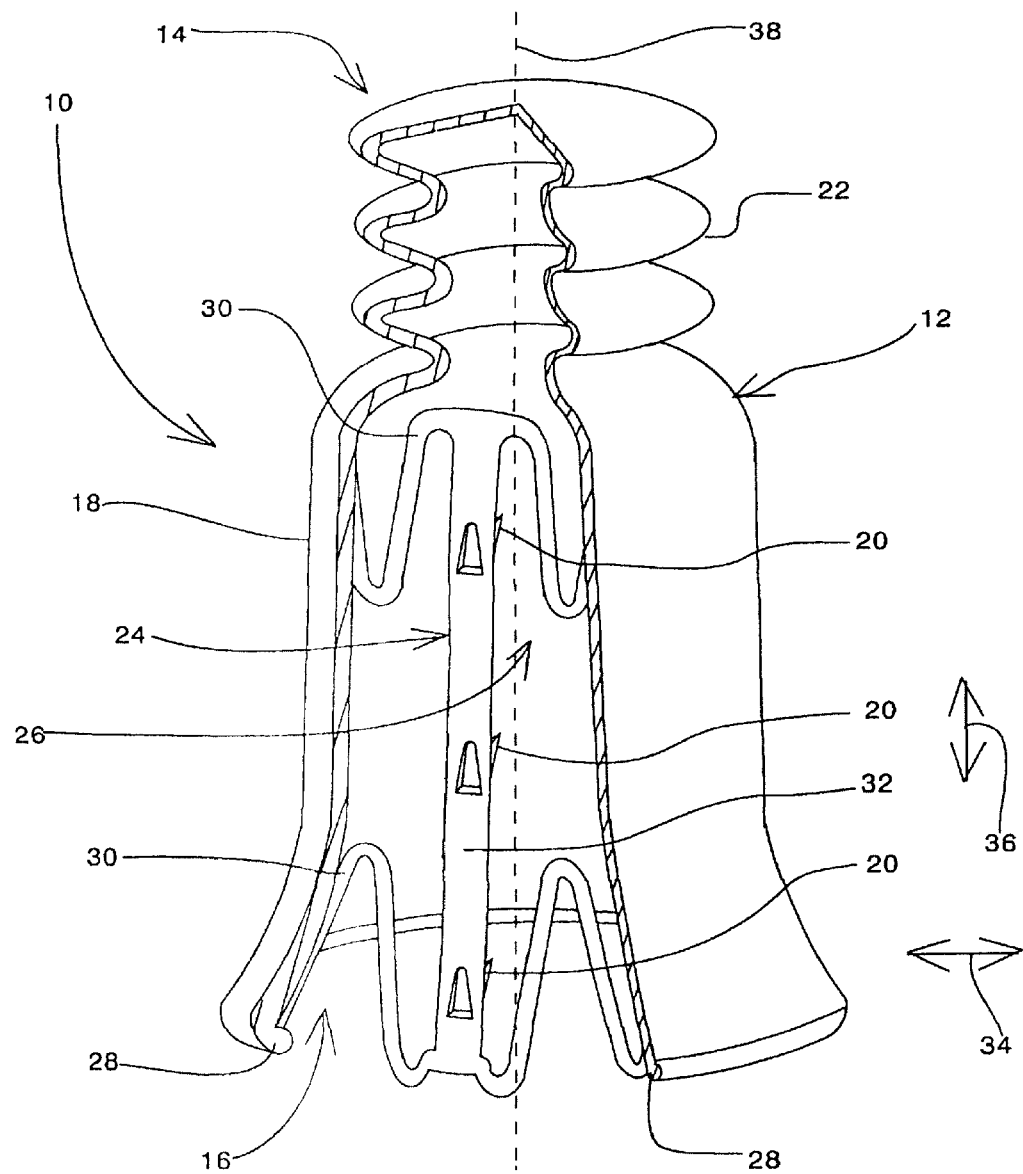
FIG. 1 shows one embodiment of a sexual misconduct perpetrator identifier cum victim body protector, according to the invention, in the form of a rapist identifier cum rape victim protector of the kind in which a carrier body as carrying tissue attachment means is integrally molded with a sheath in constituting the rapist identifier cum rape victim protector, in partly cut away three-dimensional view.

Referring to the drawings a sexual misconduct perpetrator identifier cum victim body protector in the form of a rapist identifier cum rape victim protector (in short an identifier cum protector) is generally indicated by reference numeral 10.

The identifier cum protector 10 comprises a flexible sheath 12 of liquid impermeable condom type substance extending from a closed-off inner end 14 to a mouth 16, that is divided into an outer end tissue attachment means carrying section 18 carrying tissue attachment means in the form of inwardly extending barbed tines 20 and a concertina effect formed inner end section 22. The outer end tissue attachment means carrying section 18 extends inward from the mouth 16.

The tines 20 are carried along a carrier base 24 in conjunction with which it defines an integrally formed carrier body 26. The tines 20 extend slantingly inward in facing the closed off inner end 14 of the sheath 12.

The lengths and extent of slanting of the tines 20 are selected to limit any body threatening injury to a perpetrator exposed thereto. As the section 18 sheaths the shaft part of a penis at the moment of retraction along a vagina fitted with an identifier cum protector 10 the tines 20 perform their hooking action there along leaving the sensitive glans part unaffected.

The identifier cum protector 10 is formed to be positioned against inward displacement into a body cavity of an identifier cum protector user that is exposable to a rape attack by way of an integral circumferential rib 28 extending along the mouth 16 of the sheath 12.

The carrier body 26 is of non-expansibly contractible material. It is rendered expansibly contractible by way of expansibly contractible means in the form of zigzag formed coaxially arranged circumferentially extending elements 30 that are spaced apart by linear spacers 32 from which the tines 20 extend. The length of the body 26 is naturally selected to fit the attachment means carrying section 18 of the sheath 12. The zigzag configuration enables the body 26 to be by way of a concertina type action laterally expansibly contractible, as shown by arrows 34 while also being to some extent stretchable in the linear direction, as shown by arrow 36. This feature of the body 26 ensures that it does not obstruct the expansion of the section 18, as enabled by the resilience of the sheath 18, once exposed to an action of sheath penetration. The tines 20 thus extend in sets of linear series from the spacers 32. Owing to the body 26 extending symmetrically about a central axis 38 also coinciding with the central axis of the identifier cum protector 10, the tines 20 of the various sets all face this axis 38. The inner ends of the tines 20 as being barbed, thus present hooks 40 that require professional assistance in enabling release of the identifier cum protector 10 once having become attached to the penis or other body penetrating member of a rapist.

While the tines 20 are adequately rigid to enable them to perform their hooking functions they have some resilience at the locations where their roots connect them to the base 24. In one embodiment the tines 20 are punched from the spacers 32 in a way that create such resilience. This resilience limits the tines 20 from serving as obstruction during a penetrating stroke in yielding somewhat. But during a retraction stroke the tines 20 are caused to return to their axis facing position enabling the penetration of tissue during such stroke.

The concertina effect formed inner end section 22 promotes substantial linear and some lateral expansion of the sheath 12 also co-acting with the section 18 in facilitating an overall sheath expansion thus accommodating a variety of penetrating member sizes.

Figure 2:
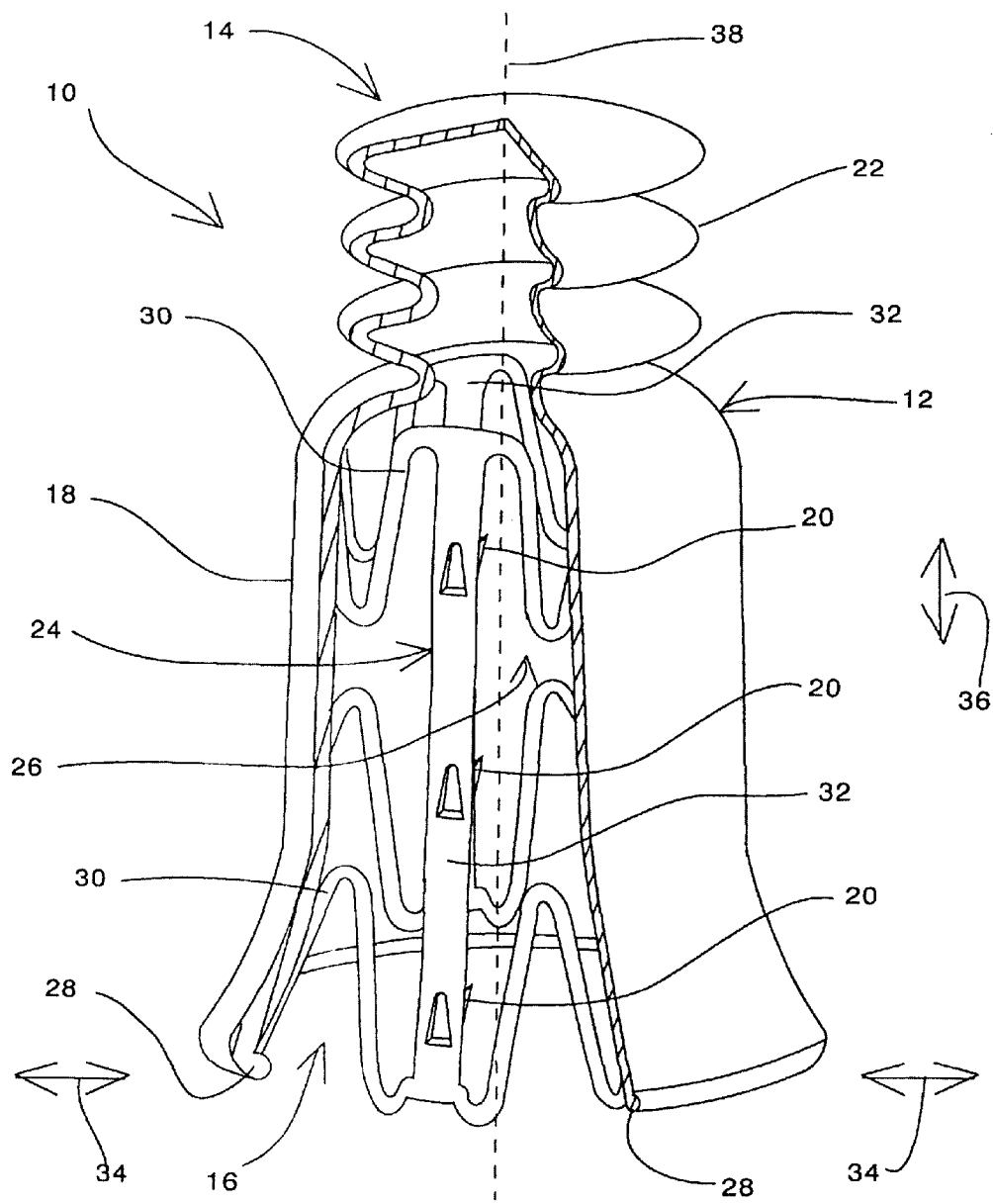
FIG. 2 shows another embodiment of the rapist identifier cum rape victim protector when of the kind in which a carrier body as carrying tissue attachment means is secured to the inside wall of the sheath, in partly cut away three-dimensional view.
Figure 3:
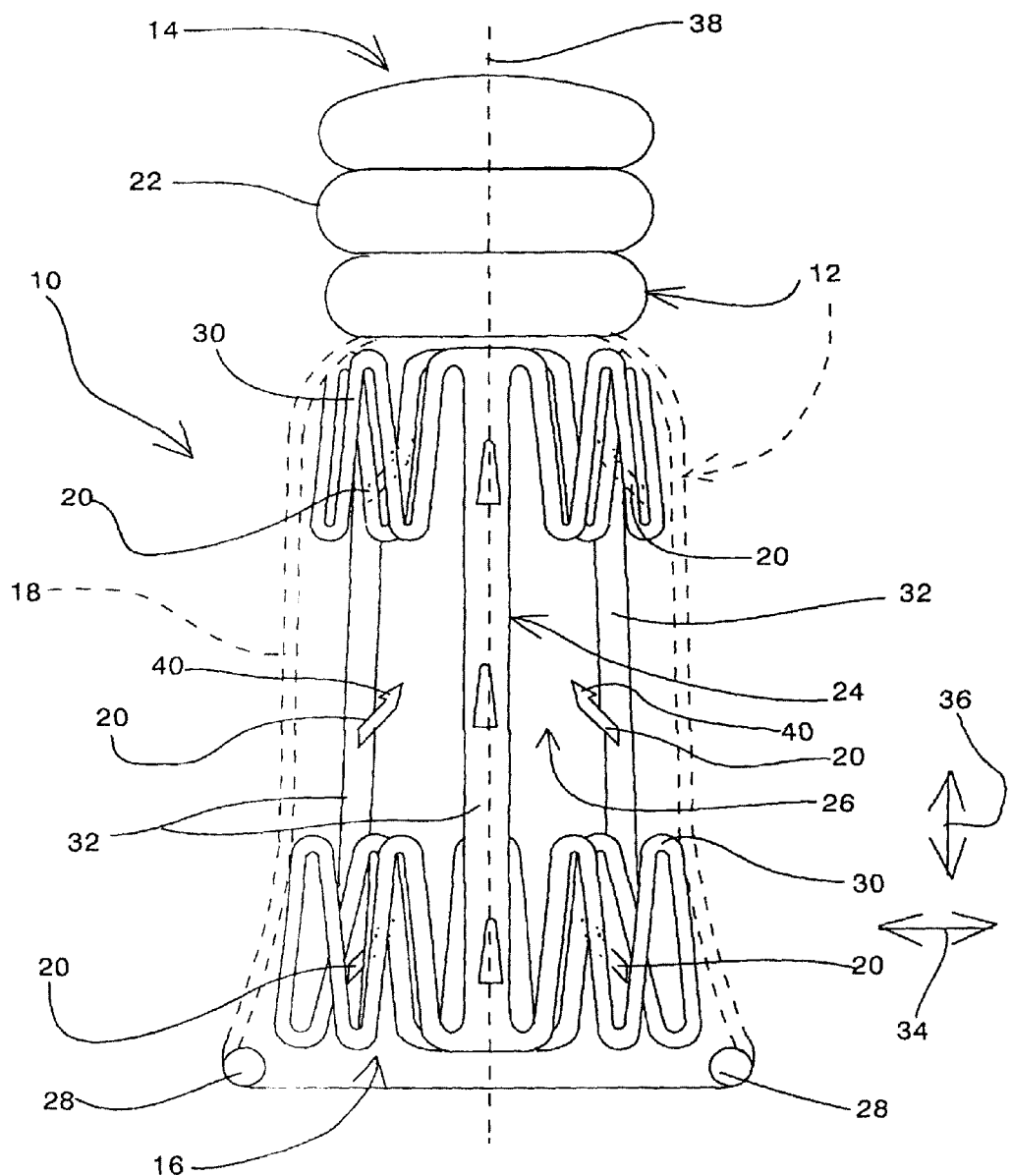
FIG. 3 shows the rapist identifier cum rape victim protector in side elevation with an identifier cum protector carrier body carrying part of the sheath shown in broke lines.
Figure 4:
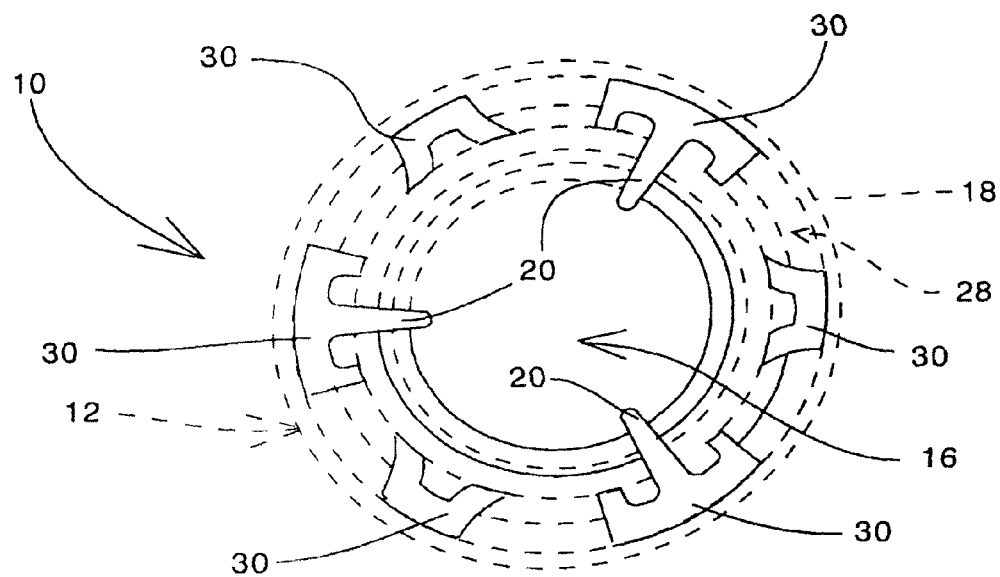
FIG. 4 shows the rapist identifier cum rape victim protector from below with the sheath shown in broke lines.

In specifically referring to FIG. 1 the body 24 can be integrally molded with the sheath 12 causing the tines 20 to extend flush from the inner wall of the sheath 12. Otherwise and referring to FIG. 2 the body 24 can be secured along the inner wall of the sheath 12 becoming glued or otherwise attached thereto during the manufacturing process.

Figure 5:
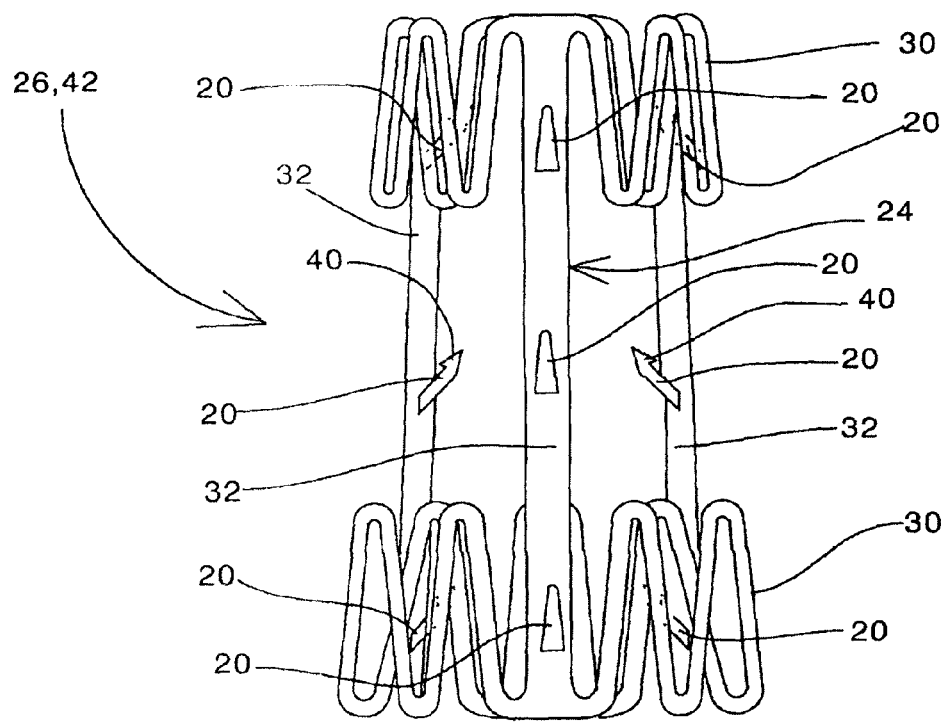
FIG. 5 shows the carrier body forming part of the rapist identifier cum rape victim protector, though also able to serve as such as a rapist identifier, in side elevation.

In further specifically referring to FIG. 5 the carrier body 26, in addition to forming part of the identifier cum protector 10, as discussed above, can also serve as identifier as such thus omitting the sheath 12 and being in the form of a rapist identifier 42.

When an identifier cum protector carrier is sexually assaulted by an attacker the sheath 12 will accommodate a large variety of penetrating member sizes owing to its ability to expand both laterally and lengthwise as brought about by the concertina effects of the inner end section 22 and the zigzag formed circumferentially extending elements 30 both naturally in conjunction with the resilience of the sheath 12 as such. During the penetrating stroke the tines 20 will yield owing to their root connected resilience thus permitting an unobstructed displacement along the sheath 12 while the possibility of any inward carrying of the full identifier cum protector 10 is limited by the functioning of the circumferential rib 28. At the end of the penetrating stroke the glans of the penis will be positioned within the non-tine carrying inner end section 22 with its shaft extending along the attachment means carrying section 18.

On retraction of the penis the tines 20 in urging inward to face the axis 38 will progressively penetrate the tissue of its shaft. The hooking effects of the hooks 40 will result in tissue catching to the extent of at least substantially preventing a perpetrator by himself releasing the identifier cum protector 10. Professional assistance in achieving such will carry the danger of exposure and subsequent identification.

To limit the possibility of substantially harming the health of a perpetrator the lengths of the tines 20 are selected to only penetrate the skin of the shaft of a penis.

It is an advantage of the invention as specifically described that an item for the identification of a rapist and in the appropriate case protection of a victim is provided that can accommodate a variety of penetrating member sizes while being held against discomfort and tine skewing once exposed to a penetrating action thus promoting its effective operation once in use. While being effective in performing its intended function(s) use of the item of the invention does not expose a perpetrator to substantial bodily injury.

What we claim is:

1. A sexual misconduct perpetrator identifier with victim body protector device for use in protecting a user and identifying a perpetrator of sexual misconduct through placement within the body cavity of a victim and linear expansion therein said body cavity upon introduction of a penetrating member therein, said device comprising a) a flexible sheath having a closed-off inner end, an opposing open mouth end, and a middle internal portion formed to be positioned against inward displacement of a body cavity of a subject user, and b) tissue attachment structures selected from tines and hooks extending inward from said internal middle portion of said sheath, wherein said tissue attachment structures provide attachment of said victim protector to said penetrating member of a perpetrator during an unauthorized penetration of said victim's body cavity in which said device is present; wherein said sheath further includes an outer attachment section ending in said mouth along which said attachment structures are situated against limiting at least the lateral expansion of said outer end attachment carrying section, and an inner end section that is arranged to at least by itself if not in conjunction with said outer end attachment carrying section enable the overall linear expansion of said device on becoming penetrated, such that said device accommodates a variety of sizes of penetrating members; wherein said flexible sheath is constructed of a liquid impermeable substance, and wherein said tissue attachment structures provide attachment of said device to the penetrating member of a perpetrator and also permits unaided release thereof from the subject body cavity to prevent serious bodily injury of such an unauthorized penetrating member of a perpetrator while also requiring specialized removal of the identifier with protector from said penetrating member, thereby allowing for exposure of identification of said perpetrator.

2. The sexual misconduct perpetrator with victim body protector device as claimed in claim 1 in which the attachment structures are carried by a flexible tissue attachment structures carrier base of which it forms part in forming a tissue attachment structures carrier body that fits the outer end attachment carrying section against any relative displacement by the carrier base being expansibly contractible in conjunction with the sheath and also against sheath enclosing zone obstruction.

3. The sexual misconduct perpetrator with victim body protector device as claimed in claim 2 in which the carrier base as of at least substantially non-expansibly contractible character is rendered expansibly contractible by way of expansibly contractible material forming part thereof accommodating at least lateral sheath expansion inclusive of during a sheath penetrating action.

4. The sexual misconduct perpetrator with victim body protector device as claimed in claim 3 in which the expansibly contractible material at least comprises coaxially arranged generally concertina effect zigzag formed circumferential elements that are interspaced by spacers along the latter of which the tissue attachment structures are found, the zigzag effect of the elements accommodating at least lateral sheath expansion inclusive of during a sheath penetrating action.

5. The sexual misconduct perpetrator with victim body protector device as claimed in claim 4 in which the attachment structures at least in so far as being in a plurality of tines extend into the zone enclosed by the outer end attachment carrying section from the spacers.

6. The sexual misconduct perpetrator with victim body protector device as claimed in claim 5 in which the spacers extend linearly with the tines being arranged in linear arrays.

7. The sexual misconduct perpetrator with victim body protector device as claimed in claim 2 in which said attachment structures are in the form of plurality of tines extending into the zone enclosed by the outer attachment carrying section to an adequate extent to enable tissue attachment of a penetrating member through only to a depth that does not pose a serious health damaging bodily injury while formed to limit the possibility of self-removal, the tines facing the inner end of the sheath and being of adequate yielding character to permit the unobstructed penetration of the sheath though adequately firm to perform their tissue attachment function during retraction.

8. The sexual misconduct perpetrator with victim body protector device as claimed in claim 7 in which the tines are formed to limit the possibility of self-removal by their inner ends being barbed.

9. The sexual misconduct perpetrator with victim body protector device as claimed in claim 7 in which the attachment structures are integrally formed with the tissue attachment carrier base in constituting the tissue attachment structures carrier body that is as such unified with the sheath forming the identifier with protector in the appropriate case becoming so unified during the process of the molding the sheath.

10. The sexual misconduct perpetrator with victim body protector device as claimed in claim 2 in which the tissue attachment structures carrier base fits the outer end attachment carrying section against any relative displacement by being either integrally formed therewith or secured thereto along its inside face.

11. The sexual misconduct perpetrator with victim body protector device as claimed in claim 1 in which said inner end section is arranged to at least by itself if not in conjunction with the outer attachment carrying section enable the overall linear expansion of the sheath through a concertina effect structure.

12. The sexual misconduct perpetrator with victim body protector device as claimed in claim 1 in which said tissue attachment structures carrying section carries the attachment structures against limiting both its lateral and linear expansion.

13. The sexual misconduct perpetrator with victim body protector device as claimed in claim 1 in which the sheath is constrained against inward displacement into a body cavity once the identifier with protector as worn is subject to a body cavity sexual misconduct penetrating involving action by the mouth of the sheath being bordered by an integrally extending circumferential rib that is formed to retain it outside a relevant body cavity even when the identifier with protector as worn is exposed to an inward urging action.

14. A sexual misconduct perpetrator identifier with victim body protector device for use in protecting a user and identifying a perpetrator of sexual misconduct comprising tissue attachment structures selected from tines and hooks extending inward from a not necessarily fully circumferentially closed-off generally tubular extending flexible tissue attachment structures carrier base for the attaching the identifier against perpetrator unaided release though also against serious health damaging of a penetrating member of a perpetrator on performing an unauthorized act of body cavity penetration of a cavity fitted with the identifier facilitating perpetrator exposure on requiring specialized removal of the identifier; characterized in that the carrier base is arranged to be at least laterally expansibly contractible enabling the accommodation of a variety of different penetrating members sizes, wherein said carrier base of a substantially non-expansibly contractible character is rendered expansibly contractible by way of expansibly contractible material forming part thereof.

15. The sexual misconduct perpetrator identifier of claim 14 in which the attachment structures integrally form part of the carrier base in forming a tissue attachment structures carrier body.

16. The sexual misconduct perpetrator with victim body protector device as claimed in claim 15 in which the tines are formed to limit the possibility of self-removal by their inner ends being barbed.

17. The sexual misconduct perpetrator with victim body protector device as claimed in claim 14 in which the tissue attachment structures are in the form of plurality of tines extending into the zone enclosed by carrier base to an adequate extent to enable tissue attachment of a penetrating member through only to a depth that does not pose a serious health damaging bodily injury while formed to limit the possibility of self-removal, the tines facing the inner end of the sheath and being of adequate yielding character to permit the unobstructed penetration of the sheath though adequately firm to perform their tissue attachment function during retraction, and in the case of the carrier base including spacers the tines thus extending there from.

18. The sexual misconduct perpetrator with victim body protector device as claimed in claim 17 in which the spacers extend linearly with the tines being arranged in linear arrays.

19. The sexual misconduct perpetrator identifier of claim 14 in which the expansibly contractible material at least comprises coaxially arranged generally concertina effect zigzag formed circumferential elements that are interspaced by spacers along the latter of which the tissue attachment structures are found, the zigzag effect of the elements accommodating at least lateral sheath expansion.

* * * * *